United States Patent [19]

Fuhlhage

[11] 4,235,807
[45] Nov. 25, 1980

[54] SYNTHESIS OF 2,6-DISUBSTITUTED BENZONITRILES

[75] Inventor: Donald W. Fuhlhage, Tonganoxie, Kans.

[73] Assignee: Thompson-Hayward Chemical Company, Kansas City, Kans.

[21] Appl. No.: 54,208

[22] Filed: Jul. 2, 1979

[51] Int. Cl.³ .................. C07C 120/00; C07C 121/52
[52] U.S. Cl. ......................... 260/465 G; 260/465 F; 260/465 R; 204/158 HA
[58] Field of Search ............ 260/465 G, 465 R, 465 F

[56] References Cited

U.S. PATENT DOCUMENTS

| 3,129,260 | 4/1964 | Yates et al. .................. 260/465 G X |
| 3,225,081 | 12/1965 | Koopman et al. ............... 260/465 G |

OTHER PUBLICATIONS

Hunt, Chemistry and Industry, p. 1873, Nov. 18, 1961.

*Primary Examiner*—Dolph H. Torrence
*Attorney, Agent, or Firm*—Norman N. Spain

[57] ABSTRACT

A one step method of converting 2,6-disubstituted benzaldehydes to 2,6-disubstituted benzonitriles which comprises heating benzaldehyde in the presence of a hydroxylamine and a dehydrating agent for about 1 to 40 hours at a temperature of 110°–250° and then separating out the resultant 2,6-disubstituted benzonitrile.

9 Claims, No Drawings

SYNTHESIS OF 2,6-DISUBSTITUTED BENZONITRILES

BACKGROUND OF THE INVENTION

This invention relates to a novel synthesis of 2,6-disubstituted benzonitriles from 2,6-disubstituted benzaldehydes.

In a conventional synthesis of 2,6-disubstituted benzonitriles from the corresponding 2,6-disubstituted benzaldehydes a two step process is involved in which the aldehyde is first converted to the corresponding oxime. The oxime is then isolated from the mixture and dried, and then the dried oxime is subjected to a dehydrating reagent such as phosphorous oxychloride.

Although frequently high yields can be achieved by the use of this process (in the case of 2,6-dichlorobenzaldehyde yields of approximately 90% of 2,6-dichlorobenzonitrile being achieved) the necessity for employing expensive equipment, the increased expenditure of man-hours and the increased time involved when a two-step process is employed renders a one-step process to be highly desirable.

However, although a one step conversion of aldehyde to nitrile has been employed for an analogous compound, the conversion of 2,4-dichlorobenzaldehyde to 2,4-dichlorobenzonitrile, as reported by J. H. Hunt Chemistry and Industry, November 18, 1961, page 1873 such as a small yield was obtained, (30%) that it would appear that the utilization of a one step conversion of the 2,6-disubstituted benzaldehyde to the 2,6-disubstituted benzonitrile would yield equally poor results.

It is an object of this invention therefore to provide a one step method of synthesis of 2,6-disubstituted benzonitriles from 2,6-disubstituted benzaldehydes in which a good yield of the 2,6-disubstituted benzonitrile is achieved.

Another object of this invention is to provide a one step method for the synthesis of 2,6-dichlorobenzonitrile, a well known herbicide from the corresponding benzaldehyde.

These and other objects of the invention will be apparent from the description that follows.

BRIEF SUMMARY OF THE INVENTION

According to the invention it has been unexpectedly discovered that 2,6-disubstituted benzonitriles may be synthesized at a high yield by conversion of 2,6-disubstituted benzaldehyde without separating the intermediate oxime from the reaction mixture.

More particularly according to the method of the invention a 2,6-disubstituted benzaldehyde in which the substitutents are groups larger than fluorine is heated together with a hydroxylamine and a dehydrating agent. Preferably the reaction is carried out at a temperature of about 110°–250° C. for a time of about 1 to 40 hours.

Examples of benzaldehydes that may be employed are those 2,6-disubstituted benzaldehydes in which the substitutents are selected from the group consisting of chlorine, bromine, iodine, alkyl of 1–6 carbon atoms such as methyl, propyl, butyl and pentyl, alkoxy of 1–6 carbon atoms such as methoxy, and butoxy, and halogenated alkyls of 1–6 carbon atoms such as trifluromethyl.

As examples of the hydroxylamine compounds that may be employed are hydroxylamine sulfate, hydroxylammonium acid sulfate or hydroxylammonium acid chloride.

As the dehydrating agent acetic anhydride or other dehydrating agents such as propionic anhydride, phosphorous pentoxide or dimethyl acetal may be employed.

The reaction is generally carried out in an organic acid solution. Salts of a weak acid are used to liberate the hydroxylamine from the salt. Such well known salts as sodium bicarbonate, sodium carbonate and potassium acetate may be employed. However sodium acetate is preferred. As the organic acid employed for use as a solvent acetic acid, propionic acid, or mixed isomers of dichlorobenzoic acids are especially useful.

DETAILED DESCRIPTION OF THE INVENTION

The invention will be described in greater detail with reference to the following examples.

EXAMPLE 1

A mixture of 3.7 g of hydroxylamine sulphate, 7 g of sodium acetate trihydrate, 17 g of acetic anhydride, 5 ml of acetic acid and 4.5 g of 2,6-dichlorobenzaldehyde was heated at reflux for 34 hours. Cooling, filtration and washing with water gave 2.7 g of pure 2,6-dichlorobenzonitrile. Stripping of the filtrate gave an additional 1 gram of pure 2,6-dichlorobenzontirile thus producing an overall yield of 84%.

EXAMPLE 2

Toluene was chlorinated employing a ferric chloride catalyst. The resultant dichlorotoluene mixed isomers were separated from monochloro and trichloro fractions by distillation. The dichlorotoluene fraction was chlorinated in the presence of ultraviolet radiation to give a mixture of 2,6-dichlorobenzalchloride and mixed dichlorobenzotrichlorides, 29 grams of this mixture was then hydrolized with sulfuric acid to produce 23 grams of a mixture of 2,6-dichlorobenzaldehyde and mixed dichlorobenzoic acids. This mixture was then refluxed overnight with 7 grams of hydroxylamine sulphate, 14 grams of sodium acetate trihydrate and 34 ml of acetic anhydride. Acetic acid and acetic anhydride were removed by distillation. Steam distillation of the residue yielded 2.7 grams of pure 2,6-dichlorobenzonitrile.

While I have thus described my invention with specific examples and applications, other modifications thereof will be apparent to those skilled in the art without departing from the spirit and scope of my invention as defined in the appended claims.

What is claimed is:

1. A method of producing 2,6-disubstituted benzonitriles from the corresponding 2,6-disubstituted benzaldehydes wherein the substituents on the 2 and 6 positions are selected from the group consisting of chlorine, bromine, iodine, alkyl of 1–6 carbon atoms, alkoxy of 1–6 carbon atoms and halogenated alkyls of 1–6 carbon atoms, comprising heating said 2,6-disubstituted benzaldehydes together with a hydroxylamine and a dehydrating agent in an organic acid solvent therefore and then separating out the resultant 2,6-disubstituted benzonitrile.

2. The method of claim 1 wherein the 2,6-benzaldehyde is 2,6-dichlorobenzaldehyde and the resultant 2,6-disubstituted benzonitrile is 2,6-dichlorobenzonitrile.

3. The method of claim 2 wherein the 2,6-dichlorobenzaldehyde is heated in the presence of hydroxylamine sulphate, acetic acid and acetic anhydride in the presence of sodium acetate.

4. The method of claim 3 wherein the mixture is heated for 1–40 hours.

5. The method of claim 2 wherein the 2,6-dichlorobenzaldehyde is heated in the presence of one or more isomers of dichlorobenzoic acids or their sodium salts, hydroxylamine sulphate, sodium acetate and acetic anhydride.

6. The method of claim 1 wherein the dehydrating agent is selected from the group consisting of acetic anhydride, propionic anhydride, phosphorous pentoxide and dimethyl acetal.

7. The method of claim 6 wherein the organic acid is an acid selected from the group consisting of acetic acid, propionic acid and mixed isomers of dichlorobenzoic acid.

8. A method of producing 2,6-dichlorobenzonitrile comprising the steps:
 (a) chlorinating toluene in the presence of a suitable chlorination catalyst to produce a mixture of dichlorinated derivatives of toluene including mixed isomers of dichlorotoluene;
 (b) separating out from said mixture the dichlorotoluene mixed isomers;
 (c) chlorinating said dichlorinated toluene mixed isomers in the presence of ultra-violet radiation to produce a mixture of 2,6-dichlorobenzalchloride and mixed dichlorobenzotrichlorides;
 (d) hydrolyzing said mixture of 2,6-dichlorobenzalchloride and dichlorobenzotrichlorides with a mineral acid to produce thereby a mixture of 2,6-dichlorobenzaldehyde and mixed dichlorobenzoic acids;
 (e) heating said mixture of 2,6-dichlorobenzaldehyde and mixed dichlorobenzoic acids in the presence of a hydroxylamine, sodium acetate and acetic anhydride;
 (f) removing acetic anhydride and the resultant acetic acid from said 2,6-dichlorobenzaldehyde containing mixture; and
 (g) separating from the resultant residue 2,6-dichlorobenzonitrile.

9. The method of claim 8 wherein the mixture is heated for 1 to 40 hours at a temperature of 110°–250° C.

* * * * *